United States Patent [19]

Rizvi et al.

[11] Patent Number: 4,512,182
[45] Date of Patent: Apr. 23, 1985

[54] GELATION MEASURING APPARATUS AND METHOD

[75] Inventors: Syed S. H. Rizvi; Patricia W. Gossett, both of Ithaca, N.Y.

[73] Assignee: Cornell Research Foundation, Inc., Ithaca, N.Y.

[21] Appl. No.: 498,386

[22] Filed: May 26, 1983

[51] Int. Cl.³ .................................................. G01N 33/02
[52] U.S. Cl. ..................................................... 73/64.1
[58] Field of Search ......................................... 73/64.1

[56] References Cited

U.S. PATENT DOCUMENTS

| 4,193,293 | 3/1980 | Cavallari | 73/64.1 |
| 4,317,363 | 3/1982 | Shen | 73/64.2 |

FOREIGN PATENT DOCUMENTS

| 325965 | 3/1972 | U.S.S.R. | 73/64.1 |
| 457011 | 2/1975 | U.S.S.R. | 73/64.1 |
| 507805 | 4/1976 | U.S.S.R. | 73/64.1 |
| 602825 | 4/1978 | U.S.S.R. | 73/64.1 |

Primary Examiner—S. Clement Swisher
Assistant Examiner—Joseph W. Roskos
Attorney, Agent, or Firm—Jones, Tullar & Cooper

[57] ABSTRACT

An apparatus and method for continuously measuring the coagulation, gelation, denaturation or other related phase transition process of food components and related biomaterials utilizing a single sample by sensing the force generated by the sample during the coagulation, gelation, denaturation or other related phase transition process thereof. A force sensing device including a sample engaging probe is provided. As the phase transition of the sample progresses, the increasing solid phase of the gelled matrix surrounds the probe and results in a continuous increase in the pressure exerted by the matrix on the probe. This force is believed to correlate with the strength of the matrix as phase transition progresses. The increased force is then measured and recorded.

13 Claims, 8 Drawing Figures

FIG.1

FIG. 2
TYPICAL PLOT OF ELECTROBALANCE FORCE VERSUS TIME OF HEATING OF ALBUMEN (pH 9.0) AT VARIOUS TEMPERATURES OF HEATING.

FIG.4
TYPICAL CURVE OBTAINED FROM THE NEW METHOD OF QUANTITATING GELATION. ELECTROBALANCE FORCE VERSUS TIME UNTILL MAXIMUM FORCE WAS EXHIBITED IS SHOWN

FIG.5
PLOT OF $\ln$ (FORCE) VERSUS TIME $(t-t_0)$ SHOWING RATE CONSTANTS $k_1, k_2$ & $t'$, THE TIME WHERE FIRST REACTION "STOPS" AND SECOND REACTION "STARTS".

FIG.7
TYPICAL PLOT OF ELECTROBALANCE FORCE VERSUS TIME OF COAGULATION FOR ENZYME-COAGULATED MILK, 30°C. THE PLOT TERMINATES AT MAXIMUM FORCE.

FIG.8
TYPICAL PLOT OF ELECTROBALANCE FORCE VERSUS TIME OF GELATION FOR GELATIN, COOLED 30 TO 1°C. THE PLOT TERMINATES AT MAXIMUM FORCE.

3
GELATION MEASURING APPARATUS AND METHOD

FIELD OF THE INVENTION

The present invention relates to an apparatus and method for continuously measuring, utilizing a force parameter, the coagulation, gelation, denaturation with different chemical reagents and other related phase transition processes as a function of time.

PRIOR ART

Gelation of food components and related biomaterials by heat, enzymes or other suitable means involves a series of complex phenomena. Most methods that observe the coagulation process involve measuring individual samples after different time intervals of heating until coagulation or gelation is completed. A popular method is to measure gel strength at various heating times (See: D. W. Hickson et al., Rheological Properties of Two Heat-Induced Protein Gels, J. Food Sci. 47: 783, 1982; and K. Shimada et al., Thermal Coagulation of Egg Albumin, J. Agric., Food Chem. 28: 409, 1980, Relationship Between Thermocoagulation of Proteins and Amino Acid Compositions, J. Agric. Food Chem. 28: 413, 1980, and Effects of Salts and Denaturants on Thermocoagulation of Proteins, J. Agric. Food Chem. 29: 15, 1981). Others have observed disappearances or appearances of different electrophoretic bands of proteins at different heating times and temperatures (See: T. Matsuda et al., Heat-induced Aggregation of Egg White Proteins as Studied by Vertical Flat-sheet Polyacrylamide Gel Electrophoresis, J. Food Sci. 46: 1829, 1981, and K. Shimada et al., 28: 409, supra). Another method is to measure the turbidity, optical density or absorbance at various wavelengths of the supernatant of centrifuged samples of protein solutions after various heat treatments (See: K. Shimada et al., 28: 409, 28: 413, and 29: 15, supra; Y. Sato et al., Functional Properties of Acetylated and Succinylated Egg White, Agric. Biol. Chem. 41: 2163, 1977; R. Nakamura et al., Factors Contributing to the Heat-induced Aggregation of Ovalbumin, Agric. Biol. Chem. 42: 819, 1978). Others measured the change in optical rotation of ovalbumin after various heating periods (See: P. O. Hegg et al., The Effect of Sodium Dodecylsulphate on the Optical Rotation of Crude Ovalbumin at Different Temperatures, J. Sci. Food Agric. 28: 103, 1977). Still another method is to measure the protein concentration or the weight of the precipitate after centrifugation of protein solutions heated to various times (See: R. Nakamura et al., 42: 819, supra; and P. O. Hegg et al., Effects of ph and Neutral Salts on the Formation and Quality of Thermal Aggregates of Ovalbumin. A Study on Thermal Aggregation and Denaturation, J. Sci. Food Agric., 30: 981, 1979). Others have observed gelation of meat batters by measuring the pressure induced by the meat batter against the pistons of a "dynamic tester" attached to an Instron Machine as a function of temperature and of time of heating (See: J. M. Schweid et al., Changes in Physical Properties of Meat Batters during Heating, J. Food Sci. 46: 850, 1981). Finally, viscosity measurements of heated samples have also been done (See: Y. Sato et al., 41: 2163, supra).

No method known to us, however, involves the continuous measurement of the heat-induced gelation process. It would be desirable to have such a method since it would eliminate the necessity of observing numerous individual samples at various time intervals throughout the gelation process, as is required by the methods noted above, and achieve the desired result with a single sample.

OBJECT AND SUMMARY OF THE INVENTION

The principal object of the present invention is to provide the existing state-of-the-art with the means for measuring the coagulation, gelation, denaturation and other related phase transition processes of food components and related biomaterials as a function of time and in a simple, versatile, nondestructive and continuous manner.

According to the invention, a probe is suspended from a force measuring and recording system and inserted into a sample. As the phase transition of the sample progresses, the increasing solid phase of the gelled matrix surrounds the suspended probe and results in a continuous increase in the pressure (force) exerted by the matrix on the probe. This force is believed to correlate with the strength of the matrix as phase transition progresses. The increased force is then measured and recorded. The measurements and recording are continuous so that a monitor is produced for tracking the progress of the phase transition.

BRIEF DESCRIPTION OF THE DRAWINGS

Eight figures have been selected for the purpose of discussion to thereby better understand this invention. These are.

DETAILED DESCRIPTION

Figure 1:
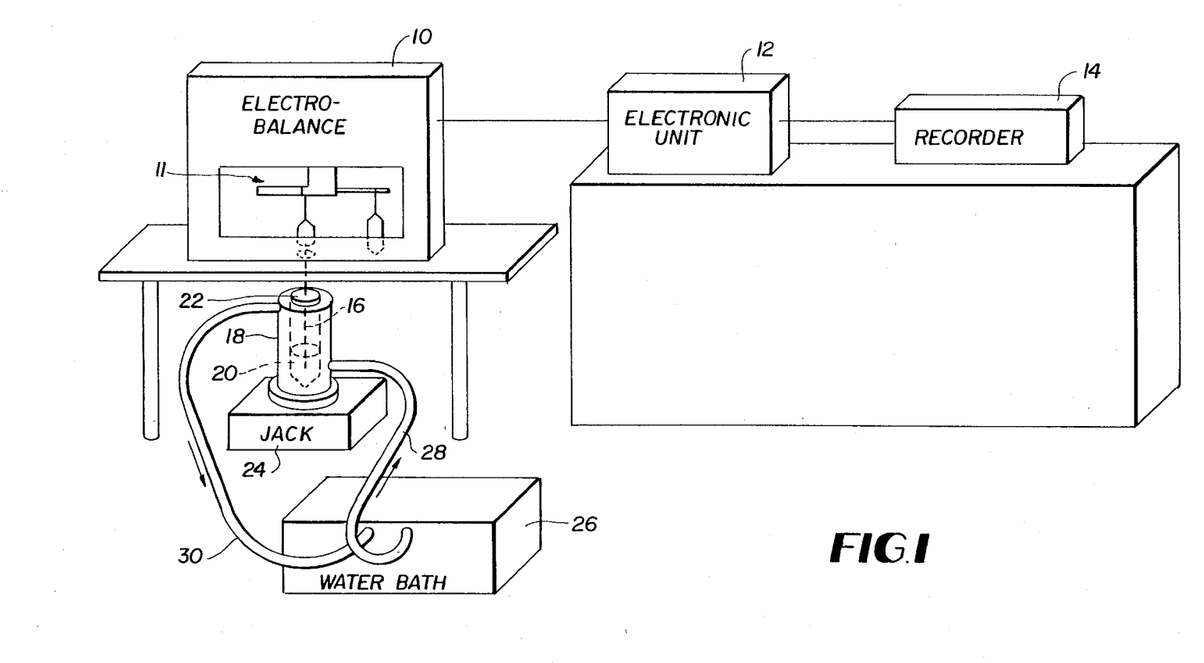
FIG. 1, which is a schematic illustration of an apparatus for continuously measuring and recording the force associated with the process of gelation for a sample.

The equipment assembled for sample analysis included a force measuring and recording apparatus. The force measuring apparatus included a Scanning Electrobalance 10, such as the Cahn model 2000, equipped with an electronic unit 12 for converting force measurements to corresponding electrical signals and a linear recorder 14, such as the Unicam AR 25, which provides a graphical analogue read-out. Alternatively, a digital read-out could be provided. The electrobalance 10 includes a balance beam 11 from which a hooked wire probe 16 is suspended. The wire probe comprises a nickel-chromium, wire cable cord, 0.508 mm in diameter, with a weight of 232 mg and a length of 135 mm. A jacketed cylinder 18 for containing a sample 20 is positioned under the electrobalance 10 so that the end of the probe is centered in the sample. The jacketed cylinder 18 is preferably 3.9 cm in diameter. A plexiglass cap 22 with a hole, preferably 3 mm in diameter, in its center through which the probe extends is placed over the top of the cylinder. A slit extending from the center hole and along a radius is also provided in the cap. The cap is employed to minimize the effect of background noise. The jacketed cylinder 18 is mounted on an adjustable jack 24 and connected with a water bath 26, such as the B. Braun Thermomix 1480, by lines 28 and 30.

The method of the present invention will be demonstrated with the equipment described above using data obtained with gelation of egg albumen at different temperatures of heating, with coagulation of milk at 30° C. and with gelation of gelatin while cooling. A number of runs were made in each instance. Prior to each run, the probe 16 was cleaned by flaming and placed on the balance beam 11 and by hanging it on the triangular hanger of the electrobalance with a pair of tweezers. Samples of 25 ml were placed into the jacketed cylinder 18. The jacketed cylinder was positioned under the electrobalance 10 by adjusting the jack 24 by means not shown. The water bath 26, preheated to the appropriate temperature, was delivered to the jacketed cylinder through line 28 and returned through line 30 by means not shown. The flow rate was approximately 1 liter/min and was controlled by appropriate valves not shown.

To initiate a run, the water bath 26 and the recorder 14 were turned on simultaneously. The samples were allowed to coagulate over a period of 30 minutes or until maximum force was observed. In separate runs, the internal temperature of each sample was measured with a thermocouple thermometer, such as the Cole-Parmer, Model 8520-50, having a 5 sec. time constant, as a function of time as coagulation occurred at the appropriate water bath temperature. This was done in an attempt to correlate the temperature of the sample with the force readings obtained as a function of time.

EGG ALBUMEN

Figure 2:
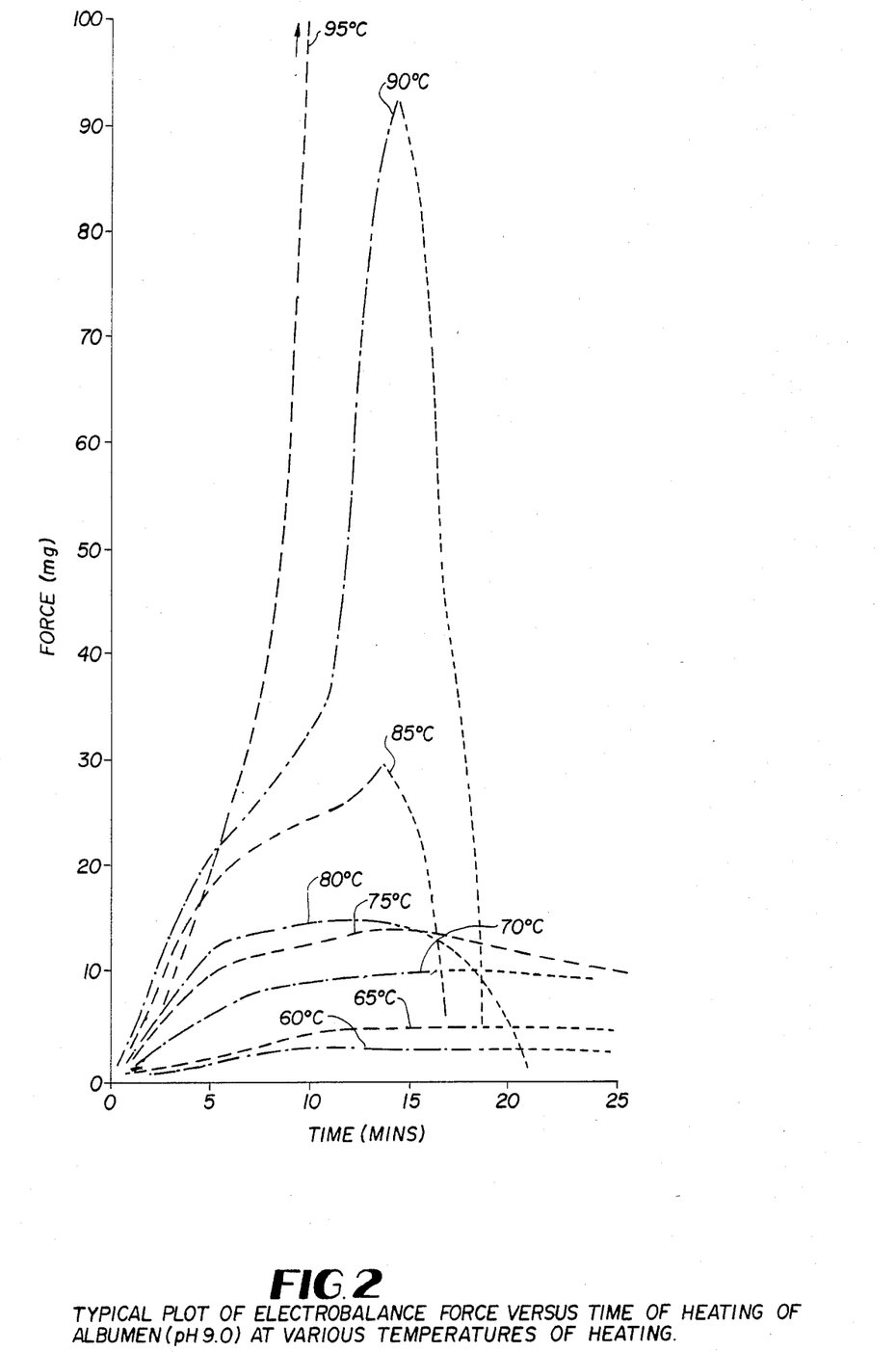
FIG. 2, which illustrates a typical plot of the measured force vs. time of testing of albumen (pH9.0) at various temperatures of heating.

Typical electrobalance force versus time curves for pH 9.0 albumen heated at different temperatures from 60° C. to 95° C. are shown in FIG. 2. As can be seen, the force increased with time until a maximum force value was attained. For treatments using 65° C. to 95° C. heating water, the force started to decrease after a maximum force was attained. The maximum force, the time required to reach this maximum force, and the internal albumen temperature at this time are shown below in Table 1.

TABLE 1

| Treatment | | Maximum Force (mg)[a] | Time (min)[a] | Internal Albumen Temperature (°C.)[b] |
|---|---|---|---|---|
| Albumen | Water Bath | | | |
| pH 9.0 | 60° C. | 3.3 ± 0.9 | 15.3 ± 1.3 | 51.3 ± 2.5 |
| " | 65 | 6.4 ± 1.8 | 15.5 ± 1.9 | 51.7 ± 1.5 |
| " | 70 | 11.3 ± 1.5 | 13.3 ± 2.7 | 55.3 ± 0.6 |
| " | 75 | 13.9 ± 2.0 | 15.4 ± 4.5 | 58.3 ± 2.1 |
| " | 80 | 14.1 ± 1.6 | 12.3 ± 2.7 | 61.7 ± 1.2 |
| " | 85 | 26.9 ± 6.6 | 12.4 ± 1.8 | 63.0 ± 1.0 |
| " | 90 | 79.9 ± 15.0 | 13.6 ± 1.5 | 68.7 ± 0.6 |

TABLE 1-continued

| Treatment | | Maximum Force (mg)[a] | Time (min)[a] | Internal Albumen Temperature (°C.)[b] |
|---|---|---|---|---|
| Albumen | Water Bath | | | |
| " | 95 | >100 | 11.1 ± 2.5 | 70.7 ± 3.1 |

[a]Quadruplicate determinations
[b]Triplicate determinations; temperature at time of peak force; measured at center.

The increase in force with time is assumed to be associated with the force exerted by the gel on the sensing probe 16 as gelation took place. The decrease in force subsequent to peak force attainment, when heating water of 65° C. or greater is used, is believed to be due to expansion of the gel once the gel is coagulated for it was observed visually that the gel had expanded to a higher point in the cylinder after coagulation. This expansion is believed to buoy the probe 16 upward thus causing a decrease in the recorded force.

Data from FIG. 2 and Table 1 indicates that as the temperature of heating increased, the force exerted by the pH 9.0 albumen increased. In general, it took less time to reach maximum force as the temperature of heating increased. The corresponding internal temperature of the albumen at peak force increased with increasing heating temperature.

Figure 3:
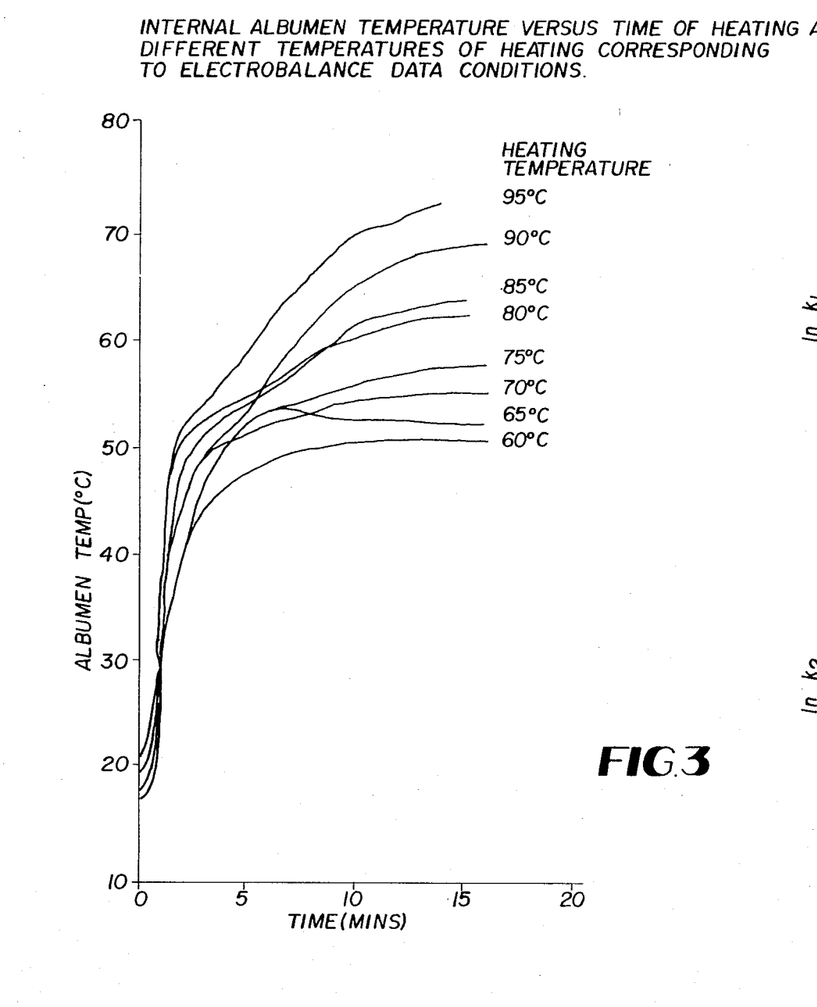
FIG. 3, which is a plot of internal albumen temperature vs. time of heating at different temperatures of heating.

In addition to electrobalance force versus time data, corresponding internal temperatures of the pH 9.0 albumen versus time data were also obtained, and the average curves for three determinations per heating temperature are shown in FIG. 3. Heat treatments with 60°, 65°, and 70° C. circulating water exhibited a final internal albumen temperature of less than 56° C. which is lower than the coagulation temperature found by P. W. Gossett in 1983 in Some Physical and Rheological Properties of Raw and Coagulated pH-Adjusted or Succinylated Egg Albumen with Respect to Water Retention Properties, Ph D. Thesis, Cornell University, Ithaca, N.Y., for pH 9.0 albumen.

In addition to the forces exerted by the gels and the internal albumen temperatures at the times peak forces are exhibited, other information might be obtained from this data by observing the rate at which peak force was attained (i.e., the shape of the force curves) for various treatments.

RATE CONSTANTS

Albumen (pH 9.0) was coagulated with 60°, 65°, 70°, 75°, 80°, 85°, 90° and 95° C. circulating water while being subjected to measurement with the electrobalance.

Figure 4:
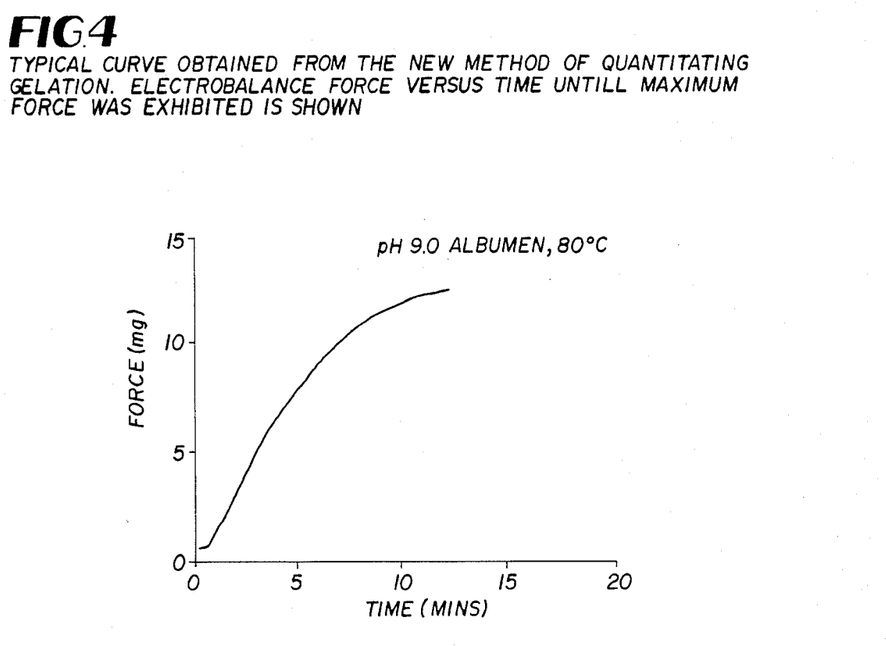
FIG. 4, which illustrates a plot of force vs. time until maximum force was exhibited.
Figure 5:
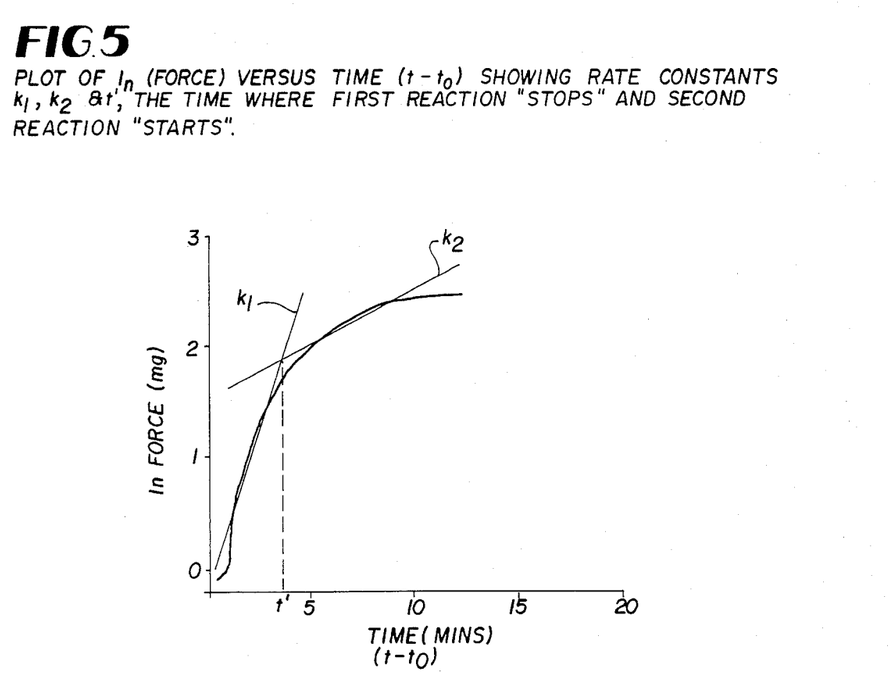
FIG. 5, which illustrates a plot of force vs. time showing rate constants $k_1$ and $k_2$ and $t'$, the time where the first step stops and the second step starts.

Initial attempts to analyze the data using first order kinetics produced a plot as shown in FIGS. 4 and 5. A curved line rather than a straight line resulted when a plot of ln (force) versus time $(t - t_0)$ was made. A plot of reciprocal force versus time (implying second order kinetics) did not yield a straight line. It was then decided to analyze the ln (force) versus time $(t - t_0)$ plots and to regress the data to yield two straight lines, with slopes $k_1$ and $k_2$, assuming first order kinetics and the existence of two steps during the heat coagulation of albumen. Average $R^2$ was $\geq 0.92$. The results of the data analysis are shown below in Table 2.

TABLE 2

| Treatment | | | | | Int. Albumen |
|---|---|---|---|---|---|
| Albumen | Water Bath | $K_1$ (min$^{-1}$)[a] | $k_2$ (min$^{-1}$)[a] | Time (min)[a,c] | Temperature |
| pH 9.0 | 60° C. | 0.329 ± 0.100[d] | 0.037 ± .008[d] | 4.83 ± 1.36 | 48.3 ± 5.0° C. |
| " | 65 | 0.377 ± 0.150[d] | 0.036 ± 0.006[d] | 5.44 ± 1.88 | 53.7 ± 0.6 |
| " | 70 | 0.421 ± 0.143[d,e] | 0.046 ± 0.012[d] | 4.42 ± 1.11 | 51.7 ± 4.9 |
| " | 75 | 0.477 ± 0.179[d,e,f] | 0.051 ± 0.011[d] | 4.54 ± 1.51 | 52.0 ± 4.4 |
| " | 80 | 0.617 ± 0.083[e,f] | 0.064 ± 0.026[d] | 3.01 ± 0.49 | 53.3 ± 3.8 |
| " | 85 | 0.662 ± 0.041[f] | 0.067 ± 0.021[d] | 3.09 ± 0.14 | 52.0 ± 5.2 |
| " | 90 | 0.690 ± 0.277[f] | 0.157 ± 0.010[e] | 2.04 ± 0.33 | 47.3 ± 7.1 |
| " | 95 | 1.233 ± 0.128[g] | 0.231 ± 0.089[f] | 1.59 ± 0.45 | 50.7 ± 4.0 |
| Ave. $R^2$ for regression | | 0.92 | 0.94 | | |

[a]Quadruplicate determinations
[b]Triplicate determinations; temperature at time as described in footnote c.
[c]Time at which first step "ends" and second step "starts".
[d,e,f,g]Means in the same column with different superscripts are significantly different at $P < 0.05$.

In addition to the rate constants $k_1$ and $k_2$, the time at which the first step "stopped" and the second step "started" was estimated by solving simultaneously the two straight line equations for time and these times are also shown in Table 2, as well as the internal albumen temperature at these times. The results showed that $k_1$ increased with increasing heating temperatures as well as $k_2$ for 90° and 95° C. heating temperatures. This was expected: the higher the temperature, the faster the reaction rate(s).

The classic picture of heat coagulation of proteins as reported by J. D. Ferry in Protein Gels, Advan. Prot. Chem. 4:2, 1948, involved a two-step sequential process where the first step was the denaturation of the proteins and the second step was the aggregation of the unfolded proteins. For our purposes it was assumed that the two processes did not overlap. In this case, $k_1$ was presumed to be the rate constant for the denaturation process, and $k_2$ the rate constant for the aggregation process. Interpretation would then be as follows: For albumen heated at various temperatures, the rates of denaturation ($k_1$) and of aggregation ($k_2$) increased with increasing heating temperature. At higher temperatures, the onset of aggregation occurred earlier implying denaturation occurred faster.

ACTIVATION ENERGIES

From Table 2 it can also be seen that the rate constants $k_1$ and $k_2$ are temperature dependent. The Arrhenius equation was used to calculate the activation energies which describe this temperature dependency of $k_1$ and $k_2$:

$$k = s\, e^{(-E_a/RT)}$$

where:
$k$ = rate constant (min$^{-1}$);
$s$ = frequency factor (min$^{-1}$);
$E_a$ = activation energy (cal/mole);
$R$ = gas constant (1.987 cal/°K. mole); and
$T$ = absolute temperature (°K.).

Figure 6:
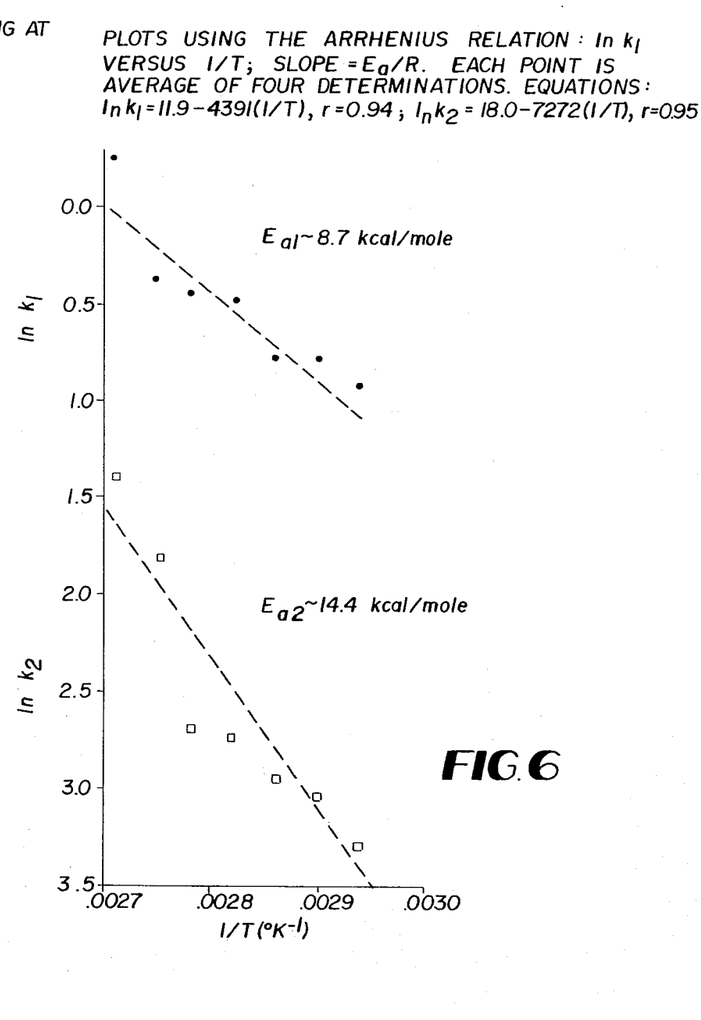
FIG. 6, which illustrates plots using the Arrhenius relation to show rate constants $k_1$ and $k_2$ vs. $1/T$. Each point is an average of four determinations.

The results of ln k versus $1/T$ plots are shown in FIG. 6. Data from heating temperatures of 65° to 95° C. were used. $E_{a1}$ was estimated to be 8.7 kcal/mole, and $E_{a2}$ to be 14.4 kcal/mole.

R. A. Dwek and G. Navon in On Boiling an Egg, Nature 240: 491, 1972, estimated the activation energies for denaturation of egg albumen between temperatures of 65° to 95° C. as being approximately 24 kcal/mole by comparing fluidities and hardness of the albumen at various temperatures.

$Z_c$ VALUE

The $Z_c$ value is defined as the heating temperature rise in °C. needed to bring about a 10-fold increase in the rate of the coagulation reaction. The problem was to somehow quantitate the coagulation process. By using the data of force versus time obtained from the electrobalance, calculation of $Z_c$ was made possible.

From FIG. 2, it was observed that at heating temperatures from 65° to 95° C., a force of at least 5 mg was exerted by the gels; from 70° to 95° C., a force of at least 10 mg was exhibited; and from 75° to 95° C., a force of at least 15 mg was shown. The times that were required to heat the gels to attain 5, 10 or 15 mg force at various temperatures of heating are shown in Table 3.

A plot of ln (heating time) to attain 5 mg force versus the heating temperature was made and linear regression of the data yielded Equation 1 in Table 3.

TABLE 3

| Heating | Heating time (min)[a] to attain: | | |
|---|---|---|---|
| Temperature | 5 mg | 10 mg | 15 mg |
| 65° C. | 10.63 ± 5.64 | — | — |
| 70 | 3.62 ± 0.93 | 9.77 ± 2.90 | — |
| 75 | 3.93 ± 1.79 | 8.05 ± 4.25 | 15.00[b] |
| 80 | 2.70 ± 0.54 | 6.54 ± 1.84 | 10.00[b] |
| 85 | 1.58 ± 0.81 | 2.97 ± 0.50 | 4.46 ± 1.07 |
| 90 | 1.89 ± 0.34 | 2.93 ± 1.29 | 4.82 ± 1.92 |
| 95 | 1.55 ± 0.62 | 3.30 ± 1.91 | 5.31 ± 2.03 |

[a]Quadruplicate determinations
[b]One observation available

Regression equations for ln (heating time) vs. heating temperature:
Eqn. (1) 5 mg: ln (Heating time) = 5.64−0.0571 (Heating temperature) Δ Heating temperature = 40.3° C.
Eqn. (2) 10 mg: ln (Heating time) = 5.96−0.0528 (Heating temperature) Δ Heating temperature = 43.6° C.
Eqn. (3) 15 mg: ln (Heating time) = 6.72−0.0651 (Heating temperature) Δ Heating temperature = 41.1° C.
$Z_c$ = average Δ heating temperature = 41.7 ± 1.7° C.

If the equation was solved for heating temperature when ln (heating time)=0 and =2.203, the difference in heating temperatures was 40.3° C. for a 10-fold increase in heating time. Similarly, a difference in heating temperature of 43.6° C. and for 41.1° C. were found for a 10-fold increase in heating time using Equations 2 and 3 (Table 3) for 10 and 15 mg, respectively. An overall average of 41.7°±1.7° C. was set equal to $Z_c$.

Literature values for $Z_c$ for various reactions vary. H. Chick and C. J. Martin in On the Heat Coagulation of Proteins, Part II. The Action of Hot Water upon Egg-Albumen and the Influence of Acid and Salts upon Reaction Velocity, J. Physiology 43: 1, 1911, estimated that the "agglutination" process of egg proteins was accelerated 2 to 2.5 time/10° C. rise in temperature. M. Dagerskod in Time-Temperature Relationships in Industrial Cooking and Frying. In: "Physical Chemical and Biological Changes in Food Caused by Thermal Processing," Hoyem, T. and Kväle, O., ed., Applied Sci. Publishers, Ltd., London pp. 77–100, 1977, quoted values of $Z_c$ ranging from 17° C. for changes in texture of cooked potatoes to 25° C. for changes in tenderness of cooked meat to 35° C. for changes in fresh appearance of sterilized peas. It appears, then, that the value of $Z_c$ (heating temperature)=41.7° C. was reasonable when compared to literature values.

MILK AND GELATIN

It was of interest to see if this new method of measuring heat-induced coagulation could be adapted to measure the coagulation of systems that: (1) were enzymatically coagulated, such as milk at 30° C., and (2) were gelled by cooling, such as gelatin from 30° to 0° C.

Figure 7:
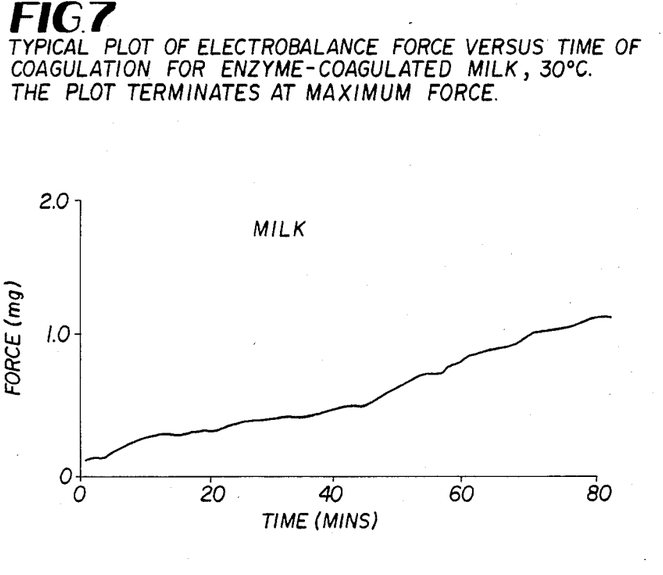
FIG. 7, which is a typical plot of force vs. time of coagulation for enzyme-coagulation milk terminating at maximum force.

The milk was coagulated as suggested by C. A. Ernstrom and N. P. Wong in Milk Clotting Enzymes and Cheese Chemistry. In: "Fundamentals of Dairy Chemistry," Webb, B. H., Johnson, A. H. and Alford, J. A. AVI publishing Co., Inc., Westport, Ct., pp. 662-771, 1974, at 30° C. and electrobalance force versus time data were obtained (FIG. 7). Increases in force were observed for about 80 min after which slight decreases in force were seen. The force readings were less than 2 mg which was much lower than those exhibited by albumen gels. Initial sample temperature was 20°±1° C. after 4 min. Plots of ln force versus time gave reasonably straight lines and one rate constant $k_{milk}$ was calculated for each determination. The average of four determinations gave $k_{milk}=0.029\pm0.007$ min$^{-1}$; the average $R^2$ for the regression lines was 0.95. Ernstrom and Wong, supra, stated that the reaction velocity of enzyme-catalyzed milk clotting was proportional to the enzyme concentration. If this is true, then treatment of the data as if the process followed first order kinetics may not be out of the question.

Figure 8:
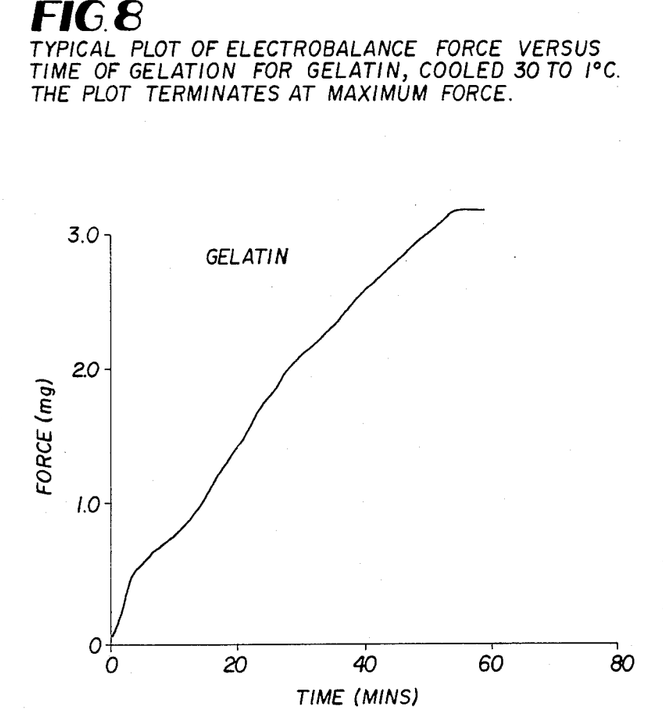
FIG. 8, which is a typical plot of force vs. time of gelation for gelatin, terminating at maximum force.

Gelatin was dissolved and gelled as described and subjected to force versus time measurements on the electrobalance (FIG. 8). The gels exerted increasing force values up to about 3.5 mg for at least 50 min after which slight decreases in force were observed. Initial sample temperature was 30°±1° C. and reached 1° C. after 14–15 min. The modulus of rigidity of gelatin gels was found by Ferry, supra, to be proportional to the square of the concentration of gelatin, implying second order kinetics. However, a plot of reciprocal force versus time did not yield a linear plot. Plots of ln (force) versus time did yield reasonably straight lines with average $R^2$ values for the regression equations of 0.94. The average of four determinations gave $k_{gelatin}=0.035\pm0.004$ min$^{-1}$. It was entirely possible that the force measured on the electrobalance was not related to the rigidity modulus and, therefore, gelation as measured by the electrobalance may follow different kinetics.

It appeared that it was possible to modify this method of measuring heat induced gelation to measure other types of coagulation or gelation processes. Conditions must be optimized, however, for each system before meaningful data can be extracted. Since these milk and gelatin gels were much "weaker" than albumen gels, perhaps a more sensitive probe can be designed. In addition, the thermal expansion characteristics of different types of gels should be considered.

What is claimed is:

1. An apparatus for continuously measuring the coagulation, gelation or denaturation of food components and related biomaterials utilizing a single sample thereof, comprising:
    a container for holding the sample;
    temperature control means connected to the container for controlling the temperature of the sample; and
    sensing means contacting the sample, said sensing means being dimensioned such that the coagulation, gelation or denaturation of the sample generates a force applied to the sensing means.

2. The apparatus as defined in claim 1, wherein the temperature control means includes a water bath which is maintained at a preselected temperature, and means for circulating the water from the bath to the container and back to the water bath.

3. The apparatus as defined in claim 1, wherein the sensing means comprises force measuring means including a pivotable mounted balance beam, and a sample engaging probe suspended from one end of the balance beam and into the sample within the container, said probe being displaced by the sample during the coagulation, gelation or denaturation further into the sample, producing thereby an unbalance at the balance beam.

4. The apparatus as defined in claim 3, wherein the sensing means further comprises measuring and recording means connected to the balance beam for converting the unbalance at the balance beam caused by the displacement of the probe into the sample into a recordable parameter and recording said parameter for visual observation.

5. The apparatus as defined in claim 3, further comprising:
    adjustment means for adjusting the position of the container relative to the probe.

6. The apparatus as defined in claim 5, wherein the temperature control means includes a water bath which is maintained at a preselected temperature, and means for circulating the water from the water bath to the container and back to the water bath, and wherein the container comprises a jacketed cylinder having an inner sample retaining chamber, an outer water circulating chamber surrounding the inner sample retaining chamber, an inlet through which water is received from the water bath and an outlet through which water passes to the water bath.

7. The apparatus as defined in claim 6, wherein the sensing means further comprises a wire by which the probe is suspended from the balance beam, and wherein the container further comprises a cap through which the wire passes into the inner sample retaining chamber for supporting the probe.

8. The apparatus as defined in claim 7, wherein the probe comprises a wire.

9. A method for continuously measuring the coagulation, gelation or denaturation of food components and related biomaterials utilizing a single sample thereof, comprising the steps of:
    confining a sample of the material to be tested;
    controlling the temperature of the sample; and
    sensing the force generated by the sample associated with the coagulation, gelation or denaturation partly by direct contact with the sample.

10. The method as defined in claim 9, wherein the step of controlling the temperature of the sample proceeds by circulating heated water past the sample, said sample being shielded from direct contact with the water.

11. The method as defined in claim 9, wherein the step of sensing the force includes recording the force for visual observation.

12. A method as defined in claim 9 wherein the step of sensing the force generated by the sample comprises suspending a probe into contact with the sample, said probe being dimensioned such that the generated force is applied to the probe.

13. An apparatus for continuously measuring the phase transition such as coagulation, gelation or denaturation of food components and related biomaterials utilizing a single sample, comprising:
  a container for holding the sample;
  temperature control means connected to the container for controlling the temperature of the sample; and
  sensing means including a probe suspended into contact with the sample, said sensing means being dimensioned such that as the phase transition of the sample progresses into an increasing solid phase of a gelled matrix, the increasing solid phase of the gelled matrix surrounds the suspended probe and results in a continuous increase in the pressure exerted by the matrix on the probe.

* * * * *